(12) United States Patent
Ueda et al.

(10) Patent No.: US 10,537,514 B2
(45) Date of Patent: Jan. 21, 2020

(54) HAIR COSMETIC COMPOSITION

(71) Applicant: HOYU CO., LTD., Nagoya-shi, Aichi (JP)

(72) Inventors: Masahisa Ueda, Nagakute (JP); Akihiro Inui, Nagakute (JP); Yuriko Kozu, Nagakute (JP)

(73) Assignee: HOYU CO., LTD., Aichi (JP)

( * ) Notice: Subject to any disclaimer, the term of this patent is extended or adjusted under 35 U.S.C. 154(b) by 0 days.

(21) Appl. No.: 15/339,321

(22) Filed: Oct. 31, 2016

(65) Prior Publication Data

US 2017/0119648 A1    May 4, 2017

(30) Foreign Application Priority Data

Oct. 30, 2015 (JP) .................................. 2015-215174
Sep. 7, 2016 (JP) .................................. 2016-174910

(51) Int. Cl.

| | | |
|---|---|---|
| *A61K 8/81* | (2006.01) | |
| *A61K 8/31* | (2006.01) | |
| *A61K 8/34* | (2006.01) | |
| *A61K 8/36* | (2006.01) | |
| *A61K 8/37* | (2006.01) | |
| *A61K 8/39* | (2006.01) | |
| *A61K 8/41* | (2006.01) | |
| *A61K 8/898* | (2006.01) | |
| *A61K 8/92* | (2006.01) | |
| *A61Q 5/08* | (2006.01) | |
| *A61Q 5/10* | (2006.01) | |

(52) U.S. Cl.
CPC ................ *A61K 8/817* (2013.01); *A61K 8/31* (2013.01); *A61K 8/342* (2013.01); *A61K 8/361* (2013.01); *A61K 8/37* (2013.01); *A61K 8/922* (2013.01); *A61K 8/925* (2013.01); *A61K 8/927* (2013.01); *A61Q 5/10* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

2006/0123564 A1* 6/2006 Nishizawa ............. A61K 8/731
8/405

FOREIGN PATENT DOCUMENTS

JP       2008-074705 A       4/2008

\* cited by examiner

*Primary Examiner* — Craig D Ricci
*Assistant Examiner* — Barbara S Frazier
(74) *Attorney, Agent, or Firm* — Norris McLaughlin, P.A.

(57) ABSTRACT

A hair color which achieves excellent texture consistently from during plain rinsing in the treatment with the hair color to the dry state after the treatment is provided includes a hair cosmetic composition containing (A) one or more cationic polymers, (B) one or more cationic surfactants with a counter ion which is chlorine or an alkyl sulfate, (C) one or more selected from hydrocarbon oils, ester oils, waxes and vegetable oils, (D) one or more nonionic surfactants and (E) one or more selected from oleyl alcohol and oleic acid.

2 Claims, No Drawings

HAIR COSMETIC COMPOSITION

BACKGROUND OF THE INVENTION

The present invention relates to a hair cosmetic composition.

In the invention, an oxidation hair dye, a hair bleach and a hair-dye-remover are generally called hair colors. The process of washing off with water (hot water) after applying a hair color during the treatment with the hair color is called "plain rinsing", and the dry state after the treatment with the hair color is called "dry state".

Each component content means "the amount of the component contained in the mixture of the agents" unless otherwise specifically noted.

Because a hair color contains an alkali agent and an oxidant such as hydrogen peroxide, the treatment with the hair color is conducted in an environment in which the texture of the hair is damaged. Thus, various components including an oily component are added to the hair color to prevent the deterioration of the texture of the hair.

However, many of the conventional hair colors do not always meet the needs of the market sufficiently in terms of the texture. For example, some hair colors provide excellent texture in the dry state, but the evaluation of the texture during plain rinsing in the treatment is not satisfactory.

JP-A 2008-074705 discloses a composition to be added to a hair treatment agent containing a fatty acid ester, an alcohol, a cationic surfactant, a nonionic surfactant and fat or oil and a hair treatment agent (a hair conditioner, a hair dye, a waving agent or a finishing agent) containing the composition to be added to a hair treatment agent. However, JP-A-2008-074705 does not disclose that a cationic polymer is added.

With the hair treatment agent according to JP-A-2008-074705, the hair is finished by rinsing and drying with a dryer after predetermined hair treatment. According to this document, various kinds of texture of the hair such as suppleness, gloss, softness, moistness, lack of tangles or friction and smoothness in the dry state after the treatment with the hair color have been evaluated, and all the items have been excellent. However, the texture of the hair during rinsing (during plain rinsing) in the treatment has not been evaluated.

Here, cationic polymers are known as components which adhere well to hair and which exhibit an excellent effect of improving the texture, and cationic polymers are generally used also in the technical field of hair colors. However, the "texture" referred to with respect to the conventional hair colors containing a cationic polymer is basically the texture in the dry state but does not mean the texture during plain rinsing.

SUMMARY OF THE INVENTION

Excellent texture of hair in the treatment with a hair color is desired not only in the dry state after the treatment with the hair color but also during plain rinsing in the treatment. As described above, however, almost no proposal concerning the problem of providing a hair color with which the texture during plain rinsing and in the dry state is improved has been made especially with respect to hair colors containing a cationic polymer, which is a typical component for improving the texture. It is believed that there are unexplained circumstances which make it difficult to improve the texture during plain rinsing with a cationic polymer in the background.

In the process of finding the unexplained circumstances, the inventors of the present application have found that "a cationic polymer, which is a hydrophilic polymer compound that adheres well to hair, provides satisfactory, excellent texture in the dry state, while in the wet state, a cationic polymer improves the texture itself but not satisfactorily". This point will be explained more specifically in the section "Advantage of the Invention" below.

Thus, based on the findings, a problem to be solved by the invention is to provide a hair color which achieves satisfactory, excellent texture consistently from during plain rinsing in the treatment with the hair color to the dry state after the treatment.

The first invention of the application for solving the above problem is a hair cosmetic composition containing the following components (A) to (E):

(A) one or more cationic polymers;

(B) one or more cationic surfactants with a counter ion which is chlorine or an alkyl sulfate;

(C) one or more selected from hydrocarbon oils, ester oils, waxes and vegetable oils;

(D) one or more nonionic surfactants; and (E) one or more selected from oleyl alcohol and oleic acid.

The second invention of the application for solving the above problem is the hair cosmetic composition according to the first invention in which the component (A) is one or more selected from polymers having a dimethyl diallyl ammonium chloride unit, cationized celluloses and cationized guar gums.

The third invention of the application for solving the above problem is the hair cosmetic composition according to the first invention in which the mass ratio of the component (D) content to the component (B) content, (D)/(B), is preferably in the range of 8.25 to 120, more preferably 15 to 100.

The fourth invention of the application for solving the above problem is the hair cosmetic composition according to any one of the first invention to the third invention in which the component (E) content is 0.5 mass % or more.

According to the first invention, the hair cosmetic composition contains the components (A) to (E), and thus a hair color which has excellent overall evaluation of the texture consistently from during plain rinsing to the dry state is obtained.

The inventors of the application have supposed that the cause of the problem of the invention described above is swelling of the component (A) in the hair in the wet state. That is, a cationic polymer which is the component (A) provides an extremely excellent effect of improving the texture in the dry state also because the cationic polymer adheres to the hair well due to the ionicity. In the wet state like during plain rinsing, however, the cationic polymer has hydrophilic property of adsorbing and holding a large amount of water. Thus, as a result of swelling of the polymer with water, the effect of improving the texture is not satisfactory although the texture becomes better than the texture when the cationic polymer is not contained.

In the process of finding out the composition of a hair color which provides satisfactory texture also in the wet state without giving up adding the component (A) (while maintaining the excellent effect of improving the texture in the dry state), the inventors of the application have found that the problem can be solved by adding the components (B) to (E) in addition to the component (A). The technical significance of the addition of the component (A) is as described above, and this point can be confirmed by comparing the evaluation of the Examples described below in the section "Examples" with the evaluation of Comparative Example 2 in which a same amount of xanthan gum, which is an anionic polymer, was added instead of the component (A).

That the components (B) to (E) are essential to solve the problem in addition to the component (A) can be confirmed from the following points. That is, the necessity of the component (B) can be confirmed by comparing the evaluation of Example 14 with the evaluation of Comparative Example 3 in which the component (B) was replaced with the same amount of an anionic surfactant. The necessity of the component (C) can be confirmed by comparing the evaluation of Example 14 with the evaluation of Comparative Example 5 which did not contain the component (C). The necessity of the component (D) can be confirmed by comparing the evaluation of the Examples with the evaluation of Comparative Example 4 which did not contain the component (D). The necessity of the component (E) can be confirmed by comparing the evaluation of the Examples with the evaluation of Comparative Example 1 in which the component (E) was replaced with the same amount of stearic acid.

The individual detailed actions of the components (B) to (E) and the interaction between the components in exhibiting the effects of the invention have not been elucidated sufficiently. However, it is speculated that through certain interaction, the components exhibit a satisfactory effect of improving the texture of the hair in the wet state and exhibit a satisfactory effect of improving the texture also in the dry state.

According to the second invention, the component (A) is one or more selected from polymers having a dimethyl diallyl ammonium chloride unit, cationized celluloses and cationized guar gums, and thus the second invention is more preferable in view of the effects of the invention.

According to the third invention, the mass ratio of the component (D) content to the component (B) content, (D)/(B), is preferably in the range of 8.25 to 120, more preferably 15 to 100, and thus the third invention is more preferable in view of the effects of the invention.

According to the fourth invention, the component (E) content is 0.5 mass % or more, and thus the fourth invention is more preferable in view of the effects of the invention.

DETAILED DESCRIPTION OF THE INVENTION

Embodiments of the invention including the best mode are explained below. The technical scope of the invention is not limited by the following embodiments.

The hair cosmetic composition of the invention is mainly composed as an oxidation hair dye, a hair bleach or a hair-dye-remover. The oxidation hair dye, the hair bleach and the hair-dye-remover contain an alkali agent and an oxidant such as hydrogen peroxide and sometimes further contain an oxidation auxiliary agent such as a persulfate.

Also, the hair cosmetic composition of the invention contains the components of (A) one or more cationic polymers, (B) one or more cationic surfactants with a counter ion which is chlorine or an alkyl sulfate, (C) one or more selected from hydrocarbon oils, ester oils, waxes and vegetable oils, (D) one or more nonionic surfactants and (E) one or more selected from oleyl alcohol and oleic acid as essential components. These components are explained in detail later.

The hair cosmetic composition which is composed as an oxidation hair dye, a hair bleach or a hair-dye-remover is generally two-agent type including a first agent containing an alkali agent and a second agent containing an oxidant but may be multiagent type which includes three agents or more and which is composed by dividing the first agent or the second agent into a plurality of agents or one-agent type. In these agents, the component (A) to the component (E) can be each added to any one agent or divided and added to a plurality of agents.

The form of the hair cosmetic composition before use is not basically limited, and known forms can be used. For example, the hair cosmetic composition can be in a solid form such as powder or a tablet or in a non-solid form such as an aqueous solution, an emulsion or gel. A solid agent is mixed with a solvent such as water before use or mixed with another agent containing a solvent such as water. The form of the hair cosmetic composition during use is basically the non-solid, but the hair cosmetic composition can be used as foam formed by known means.

[Essential Components of Hair Cosmetic Composition]
(Cationic Polymer)

The kinds of cationic polymers used as the component (A) are not limited, but examples thereof include water-soluble polymers having an amino group or an ammonium group attached to the polymer chain or having a dimethyl diallyl ammonium chloride unit. More specifically, examples thereof include polymers of diallyl quaternary ammonium salts, diallyl quaternary ammonium salt.acrylamide copolymers, cationized celluloses, cationized guar gums, cationic starch, quaternary polyvinylpyrrolidone derivatives and the like.

Of the above examples of the component (A), one or more selected from polymers having a dimethyl diallyl ammonium chloride unit, cationized celluloses and cationized guar gums are particularly preferable.

Examples of the polymers having a dimethyl diallyl ammonium chloride unit include cationic acrylamide.acrylic acid.dimethyl diallyl ammonium chloride copolymers, diallyl quaternary ammonium salt.acrylamide copolymers (Merquat 550 by The Lubrizol Corporation and the like), dimethyl diallyl ammonium chloride polymers (Merquat 100 by The Lubrizol Corporation and the like) and the like.

Examples of the cationized celluloses include hydroxyethyl cellulose dimethyl diallyl ammonium chloride (Celquat L-200 and H-100 by Akzo Nobel N.V.), Leogard G and GP by Lion Corporation, Polymer JR-125, JR-400, JR-30M, LR-400 and LR-30M by The Dow Chemical Company and the like.

Examples of the cationized guar gums include guar gum 0-[2-hydroxy-3-(trimethylammonio)propyl] chloride (commercial name; Jaguar Excel; manufactured by Sansho Co., Ltd.) and the like.

The content of the one or more kinds of the component (A) in the hair cosmetic composition is not particularly limited but is for example in the range of 0.01 to 1 mass %, preferably in the range of 0.05 to 0.5 mass %.

(Cationic Surfactant with Counter Ion which is Chlorine or Alkyl Sulfate)

The kinds of cationic surfactants with a counter ion which is chlorine or an alkyl sulfate used as the component (B) are not limited. Examples of the cationic surfactants with a counter ion which is chlorine include cetyltrimethylammonium chloride (cetrimonium chloride), behenyltrimethylammonium chloride (behentrimonium chloride), lauryltrimethylammonium chloride, stearyltrimethylammonium chloride (steartrimonium chloride), alkyltrimethylammonium chloride, distearyldimethylammonium chloride (distearyldimonium chloride), dicocoyldimethylammonium chloride and the like.

Examples of the cationic surfactants with a counter ion which is an alkyl sulfate include lanolin fatty acid amino propylethyldimethylammonium ethyl sulfate, behenyltrimethylammonium methyl sulfate and the like.

Of the above examples of the component (B), cationic surfactants having 16 carbon atoms are particularly preferable because the cationic surfactants can secure the softness of the texture of the hair during plain rinsing described above and also can secure the general effect on the texture as a cationic surfactant due to the chain lengths which are not too short. The term "having 16 carbon atoms" means that in the chemical structure of alkylmethylammonium chloride type, the carbon atom number of the saturated long-chain alkyl group in the molecule is 16. In other words, those which have a plurality of alkyl groups in the molecule and in which the total carbon atom number of the alkyl groups is 16 are not included.

The component (B) content of the hair cosmetic composition is not particularly limited but is for example in the range of 0.01 to 2 mass %, more preferably in the range of 0.05 to 1 mass %. In this regard, the mass ratio of the component (D) content (described below) to the component (B) content, D/B, is preferably in the range of 8.125 to 120, more preferably in the range of 15 to 100.

(Hydrocarbon Oil, Ester Oil, Wax and Vegetable Oil)

The kinds of hydrocarbon oils, ester oils, waxes and vegetable oils used as the component (C) are not limited. Examples of the hydrocarbon oils include liquid isoparaffin, liquid paraffin, paraffin, α-olefin oligomer, polyisobutene, hydrogenated polyisobutene, mineral oils, squalane, polybutene, polyethylene, microcrystalline wax and Vaseline.

Examples of the ester oils include myristyl myristate, cetyl 2-ethylhexanoate, diisopropyl adipate, isopropyl myristate, stearyl stearate, isotridecyl myristate, octyldodecyl ricinoleate, fatty acid having 10 to 30 carbon atoms cholesterol/lanosterol esters, cetyl lactate, acetylated lanolin, ethylene glycol di-2-ethylhexanoate, pentaerythritol fatty acid esters and the like.

Examples of the waxes include beeswax, candelilla wax, carnauba wax, jojoba oil, lanolin and the like.

Examples of the vegetable oils include grapeseed oil, olive oil, *camellia* oil, shea butter, almond oil, safflower oil, sunflower oil, soybean oil, cottonseed oil, sesame oil, corn oil, rapeseed oil, rice bran oil, rice germ oil, avocado oil, macadamia nut oil, castor oil, coconut oil, evening primrose oil and the like.

The content of the one or more kinds of the component (C) in the hair cosmetic composition is not particularly limited but is for example in the range of 0.5 to 15 mass %, more preferably in the range of 1 to 10 mass %. As it is seen from the comparison between Example 13 and the other Examples described below, a combination use of two or more kinds of the component (C) is advantageous for the effects of the invention.

(Nonionic Surfactant)

The kinds of nonionic surfactants used as the component (D) are not limited, but examples thereof include polyoxyethylene (hereinafter also referred to as POE) alkyl ethers, POE alkyl phenyl ethers, POE.polyoxypropylene (hereinafter also referred to as POP) alkyl ethers, POE sorbitan fatty acid esters, POE propylene glycol fatty acid esters, POE glyceryl monofatty acid esters, POE hydrogenated castor oil and the like. A same kind of the component (D) has different parameters such as the HLB value when the number of polymerized ethylene oxide molecules is different. Other examples of the component (D) include alkylol amides, POE fatty acid amides, sucrose fatty acid esters, alkyl glucosides, lecithin derivative hydrogenated soybean lecithin and the like.

The content of the one or more kinds of the component (D) in the hair cosmetic composition is not particularly limited but is for example in the range of 3 to 20 mass %, preferably in the range of 5 to 15 mass %.

(Oleyl Alcohol and Oleic Acid)

The content of the one or more selected from oleyl alcohol and oleic acid used as the component (E) in the hair cosmetic composition is not particularly limited but is for example preferably in the range of 0.1 to 10 mass %, more preferably in the range of 0.5 to 5 mass %.

[Important Components Except for Essential Components in Hair Cosmetic Composition]

(Case of Oxidation Hair Dye)

The oxidation hair dye contains a first agent containing an alkali agent and an oxidation dye and a second agent containing an oxidant and dyes hair through degradation of the melanin in the hair and oxidative polymerization of the oxidation dye caused by the oxidant. Oxidation dyes are classified into dye intermediates and couplers. Except for the oxidation dye, a direct dye such as acid dyes, basic dyes, nitro dyes, natural dyes and disperse dyes can also be added.

Examples of the dye intermediates include phenylenediamines, aminophenols, toluylenediamines, diphenylamines, diaminophenylamines, N-phenylphenylenediamines, diaminopyridines and salts thereof. Examples of the salts are hydrochlorides, sulfates, acetates and the like.

Specifically, examples thereof include p-phenylenediamine, toluene-2,5-diamine, p-aminophenol, N,N-bis(β-hydroxyethyl)-p-phenylenediamine, N-(β-hydroxyethyl)-N-ethyl-p-phenylenediamine, 2-(β-hydroxyethyl)-p-phenylenediamine and salts thereof. Another example is 2,2'-[(4-aminophenyl)imino]bisethanol sulfate.

A coupler is a compound which develops a color by binding to a dye intermediate and is contained in the first agent according to the need. Examples of the coupler include resorcinol, pyrogallol, catechol, m-aminophenol, m-phenylenediamine, 2,4-diaminophenol, 1,2,4-benzenetriol, toluene-3,4-diamine, toluene-2,4-diamine, hydroquinone, a-naphthol, 2,6-diaminopyridine, 1,5-dihydroxynaphthalene, 5-amino-o-cresol, p-methylaminophenol, 2,4-diaminophenoxyethanol, gallic acid, tannic acid, ethyl gallate, methyl gallate, propyl gallate, gallnut, 5-(2-hydroxyethylamino)-2-methylphenol and salts thereof.

The dye intermediate content of the oxidation hair dye is preferably 0.01 to 10 mass %, more preferably 0.1 to 5 mass %.

The first agent may appropriately contain at least one kind selected for example from oxidation dyes included in "The Japanese Standards of Quasi-Drug Ingredients 2006 Consolidated Edition (issued on Nov. 25, 2013, Yakuji Nippo Limited)" and direct dyes as a dye other than the oxidation dye.

An alkali agent promotes the action of the oxidant contained in the second agent and improves the dyeing property by swelling the hair and improving the penetration of the dye to the hair. Examples of the alkali agent include ammonia, alkanolamines, organic amines, inorganic alkalis, basic amino acids and sulfates. Examples of organic amines include 2-amino-2-methyl-1,3-propanediol and guanidine. Examples of inorganic alkalis include sodium hydroxide, potassium hydroxide, sodium carbonate, potassium carbonate, ammonium carbonate, sodium bicarbonate and ammonium bicarbonate. Examples of basic amino acids include arginine, lysine and salts of basic amino acids. Examples of the salts of basic amino acids include ammonium salts. An example of sulfates is ammonium sulfate.

To secure the action of hydrogen peroxide and to inhibit hair damage for example, the alkali agent content is preferably an amount with which the pH of the oxidation hair dye obtained by mixing the first agent and the second agent is in the range of 6 to 12.

The second agent contains at least an oxidant. The oxidant causes oxidative polymerization of the oxidation dye to develop a color. Examples of the oxidant include hydrogen peroxide, urea peroxide, melamine peroxide, sodium percarbonate, potassium percarbonate, sodium perborate, potassium perborate, sodium peroxide, potassium peroxide, magnesium peroxide, barium peroxide, calcium peroxide, strontium peroxide, a sulfate-hydrogen peroxide adduct, a phosphate-hydrogen peroxide adduct and a pyrophosphate-hydrogen peroxide adduct.

The oxidant content of the oxidation hair dye is preferably 0.1 to 10.0 mass %, particularly preferably 0.5 to 8.0 mass %, from the viewpoints of sufficient oxidative polymerization of the oxidation dye, inhibition of hair damage and the like.

(Case of Hair Bleach)

The hair bleach contains a first agent containing an alkali agent and a second agent containing an oxidant, and the hair bleach degrades the melanin in the hair and bleaches the hair. The hair bleach is composed basically in a similar manner as the oxidation hair dye except that the hair bleach does not contain an oxidation dye.

(Case of Hair-Dye-Remover)

The hair-dye-remover is generally multiagent type containing two agents or more, and purposes thereof are to bleach the hair and remove the hair dye (degrade the dye adhered to the hair). When compared with the hair bleach, a difference is that an alkali agent is added to the first agent and also an oxidation auxiliary agent such as a persulfate is further added.

Preferable examples of the persulfate are persulfates of alkali metals, and an especially preferable example thereof is potassium persulfate or sodium persulfate. The persulfate content of the hair-dye-remover is not limited but is preferably in the range of 2.0 to 25 mass %, more preferably in the range of 3.5 to 18 mass %.

[Optionally Added Components]

(Polymers Other than Component (A))

Polymers other than the component (A) are nonionic polymers, anionic polymers and amphoteric polymers. The content of these polymers in the hair cosmetic composition is not limited but is preferably in the range of 0.01 to 5 mass %. Examples of the nonionic polymers include hydroxyethyl cellulose, hydroxypropylmethyl cellulose, hydroxypropyl cellulose, methyl cellulose, dextrin, galactan, pullulan, highly polymerized polyethylene glycol, polyvinyl alcohol, vinylpyrrolidone, acrylic acid and methacrylic acid esters, copolymers of acrylamide and methacrylamide, polyacrylamide having a molecular weight of 100,000 or more, dimethylhydantoin formaldehyde resin and the like.

Examples of the anionic polymers include xanthan gum, carrageenan, sodium alginate, pectin, furcellaran, gum Arabic, gum ghatti, gum karaya, gum traganth, agar powder and the like. Other examples are carboxymethyl cellulose obtained by introducing a carboxymethyl group to cellulose and the like.

Examples of the amphoteric polymers include Polyquaternium-22, Polyquaternium-47 and Polyquaternium-53. Moreover, examples thereof include N-methacryloyl ethyl N,N-dimethylammonium a-N-methylcarboxy betaine.butyl methacrylate copolymers, hydroxypropyl acrylate.butylaminoethyl methacrylate.octylamide acrylate copolymers and the like.

(Surfactants Other than Components (B) and (D))

Surfactants other than the components (B) and (D) are cationic surfactants other than the component (B), anionic surfactants and amphoteric surfactants. The content of these surfactants in the hair cosmetic composition is not limited but is preferably in the range of 0.01 to 10 mass %. Examples of the cationic surfactants other than the component (B) include quaternary ammonium salt cationic surfactants with a counter ion which is bromine, such as cetyltrimethylammonium bromide and stearyltrimethylammonium bromide. Other examples are stearyltrimethylammonium saccharin, cetyltrimethylammonium saccharin and the like.

Examples of the anionic surfactants include alkyl ether sulfates such as sodium POE lauryl ether sulfate, alkyl sulfates such as sodium lauryl sulfate, sodium cetostearyl sulfate and sodium cetyl sulfate, alkenyl ether sulfates, alkenyl sulfates, olefin sulfonates, alkane sulfonates, saturated or unsaturated fatty acid salts, alkyl or alkenyl ether carboxylates, a-sulfone fatty acid salts, N-acylamino acid surfactants such as triethanolamine cocoyl glutamate (TEA cocoyl glutamate), phosphate mono- or di-ester surfactants, sulfosuccinate esters and the like. The counter ions of the anionic groups of the surfactants are for example sodium ion, potassium ion and triethanolamine.

Examples of the amphoteric surfactants include fatty acid amidopropyldimethylaminoacetic acid betaine (for example, coconut oil fatty acid amidopropyldimethylaminoacetic acid betaine), alkyldimethylaminoacetic acid betaine (for example, lauryldimethylaminoacetic acid betaine), N-acylaminoethyl-N-2-hydroxyethylamino carboxylates (for example, Na cocoamphoacetate (N-coconut oil fatty acid acyl-N'-carboxymethyl-N'-hydroxyethyl ethylene diamine)), N-acylaminoethyl-N-carboxymethoxyethyl amino carboxylates (for example, Na cocoamphodiacetate), hydroxyalkyl(C12-14) hydroxyethyl sarcosine and the like.

(Oily Components Other than Components (C) and (E))

Oily components other than the components (C) and (E) are higher alcohols except for oleyl alcohol, silicones, fats or oils except for vegetable oils, higher fatty acids except for oleic acid, alkyl glyceryl ethers and the like. The content of these components in the hair cosmetic composition is not limited but is preferably in the range of 3 to 20 mass %.

Examples of the higher alcohols except for oleyl alcohol include lauryl alcohol, 2-octyldodecanol, isostearyl alcohol, hexyldecanol, linoleyl alcohol, myristyl alcohol, cetyl alcohol, stearyl alcohol, cetostearyl alcohol, behenyl alcohol, arachyl alcohol, lanolin alcohol and the like.

Examples of the silicones include dimethylpolysiloxane (INCI name: dimethicone), dimethylpolysiloxane having a hydroxy end group (INCI name: dimethiconol), methylphenylpolysiloxane, decamethylcyclopentasiloxane, polyether-modified silicones, amino-modified silicones, betaine-modified silicones, alkyl-modified silicones, alkoxy-modified silicones, mercapto-modified silicones, carboxy-modified silicones, fluorine-modified silicones and the like. Examples of polyether-modified silicones include POE.methylpolysiloxane copolymers (PEG-10 dimethicone) and the like.

Examples of the fats or oils except for vegetable oils include beef tallow and the like.

Examples of the higher fatty acids except for oleic acid include lauric acid, myristic acid, palmitic acid, stearic acid, behenic acid, isostearic acid, 12-hydroxystearic acid, lanolin fatty acid and the like.

Examples of the alkyl glyceryl ethers include batyl alcohol, chimyl alcohol, selachyl alcohol, isostearyl glyceryl ether and the like.

A pH-adjusting agent, a sugar, a solvent, a polyhydric alcohol, a chelating agent, a dispersant, a stabilizer, a plant extract, a crude drug extract, a vitamin, a fragrance, an ultraviolet absorber or the like may be appropriately selected and added to the hair cosmetic composition in addition to the above components.

(Polyhydric Alcohol)

Examples of the polyhydric alcohol include ethylene glycol, diethylene glycol, triethylene glycol, polyethylene glycol, propylene glycol, dipropylene glycol, isoprene glycol, 1,3-butylene glycol, glycerol, diglycerol, polyglycerol and the like.

EXAMPLES

The Examples and the Comparative Examples of the invention are explained below. The technical scope of the invention is not limited by the Examples and the Comparative Examples.

[Compositions of Two-Agent-Type Hair Bleach and Two-Agent-Type Oxidation Hair Dye]

The first agents of the two-agent-type hair bleach having the respective compositions according to Examples 1 to 14 shown in Table 1 at the end were prepared in accordance with a general method and evaluated. Also, the first agents having the compositions according to Comparative Examples 1 to 5 shown in Table 2 at the end were prepared in accordance with a general method and evaluated. The unit of the values indicating the respective component contents in Table 1 and Table 2 is mass %, and the values are the mass % amounts in each first agent.

Although it is not shown, in Examples 15 to 28 and Comparative Examples 6 to 10, oxidation hair dyes were prepared by adding the oxidation dye described below to the respective first agents of the two-agent-type hair bleach according to Examples 1 to 14 and Comparative Examples 1 to 5 and evaluated.

With respect to the components listed in Table 1 and Table 2, oleic acid and oleyl alcohol are the components (E) of the invention, and stearic acid is a component which was used for a comparison with the components (E). Hydroxyethyl cellulose dimethyl diallyl ammonium chloride and the dimethyl diallyl ammonium chloride polymer are the components (A) of the invention. Xanthan gum, which is an anionic polymer, is a component which was used for a comparison with the components (A).

Sodium polyoxyethylene lauryl ether sulfate, which is an anionic surfactant, is a component which was used for a comparison with the components (B). Polyoxyethylene(2) cetyl ether, polyoxyethylene(5.5) cetyl ether and polyoxyethylene(30) cetyl ether are all the components (D) of the invention. Moreover, liquid isoparaffin, cetyl 2-ethylhexanoate, beeswax, lanolin and olive oil are all the components (C) of the invention.

In all of the Examples and the Comparative Examples above, a second agent having the same composition was used. The composition of the second agent is shown below. The values indicating the respective component contents are the mass % amounts in the second agent.

| Composition of Second Agent | |
|---|---|
| Cetanol | 4 mass % |
| Polyoxyethylene stearyl ether | 0.5 mass % |
| Polyoxyethylene cetyl ether | 0.5 mass % |
| Sodium N-stearoyl-N-methyl taurate | 0.1 mass % |
| Hydroxyethane diphosphonic acid | 0.1 mass % |
| Tetrasodium hydroxyethane diphosphonate | 0.1 mass % |
| Phenoxyethanol | 0.1 mass % |
| 35% hydrogen peroxide | 16.5 mass % |
| Purified water | balance |

[Evaluation of Two-Agent-Type Hair Bleach]

The first agents of the two-agent-type hair bleach according to Examples 1 to 14 and Comparative Examples 1 to 5 were each mixed with the second agent having the above composition at a mass ratio of 1:1, and 30 g of the resultant compositions were each applied evenly per 10 g of hair-bundle for the evaluation of the texture. Then, the hair-bundles were left under a temperature condition of 30° C. for 30 minutes and then plain rinsed to wash off the hair bleach. The texture during washing off was evaluated.

The items of the texture which were evaluated during washing off included not only "smoothness" but also "softness (elasticity)", "thickness", "lubricity" and the like, and the texture was evaluated comprehensively. The ranks of the criteria of the evaluation were: A when "the texture is extremely good"; B when "the texture is good"; C when "the texture is neither good nor bad"; and D when "the texture is bad".

To obtain objectivity of the sensory evaluation, 10 analyzers evaluated the texture. The results of the evaluation were collected, and the most given evaluation rank of each Example or Comparative Example was used as the rank of the example. When there were two most given evaluation ranks, the lower evaluation rank was used. The results of the evaluation are shown in the cells "Texture During Washing Off" in Tables 1 and 2.

After the above evaluation, the hair-bundles for the evaluation of the texture of the Examples and the Comparative Examples after plain rinsing were washed with a shampoo and treated with a conditioner using "Promaster Color Care LX Stylish Line" (manufactured by Hoyu Co., Ltd). Then, the hair-bundles were dried with a dryer, and the texture after drying was evaluated by the same evaluation method and the same criteria as those used for the texture during washing off by the 10 analyzers. The results of the evaluation were collected and the evaluation rank of each of the Examples and the Comparative Examples was determined in a similar manner. The results of the evaluation are shown in the cells "Texture After Drying" in Tables 1 and 2.

Also when the texture was evaluated using "guar gum O-[2-hydroxy-3-(trimethylammonio)propyl] chloride", which is a cationized guar gum, instead of the component (A) of Example in Table 1, "hydroxyethyl cellulose dimethyl diallyl ammonium chloride", effects equivalent to those of Example 1 were obtained.

TABLE 1

| Component | Example 1 | Example 2 | Example 3 | Example 4 | Example 5 | Example 6 | Example 7 |
|---|---|---|---|---|---|---|---|
| Hydroxyethyl cellulose dimethyl diallyl ammonium chloride | 0.1 | 0.1 | 0.1 | 0.1 | 0 | 0.1 | 0.1 |

TABLE 1-continued

| Component | | | | | | | |
|---|---|---|---|---|---|---|---|
| Dimethyl diallyl ammonium chloride polymer | 0 | 0 | 0 | 0 | 0.1 | 0 | 0 |
| Xanthan gum | 0 | 0 | 0 | 0 | 0 | 0 | 0 |
| Cetyltrimethylammonium chloride | 0.4 | 0.4 | 0.4 | 0.4 | 0.4 | 0 | 0 |
| Behenyltrimethylammonium chloride | 0 | 0 | 0 | 0 | 0 | 0.4 | 0 |
| Cetrimonium methosulfate | 0 | 0 | 0 | 0 | 0 | 0 | 0.4 |
| Sodium polyoxyethylene lauryl ether sulfate | 0 | 0 | 0 | 0 | 0 | 0 | 0 |
| Liquid isoparaffin | 4 | 4 | 4 | 4 | 4 | 4 | 4 |
| Paraffin | 0 | 0 | 0 | 0 | 0 | 0 | 0 |
| Cetyl 2-ethylhexanoate | 1 | 1 | 1 | 1 | 1 | 1 | 1 |
| Myristyl myrisate | 0 | 0 | 0 | 0 | 0 | 0 | 0 |
| Beeswax | 0.4 | 0.4 | 0.4 | 0.4 | 0.4 | 0.4 | 0.4 |
| Lanolin | 0.4 | 0.4 | 0.4 | 0.4 | 0.4 | 0.4 | 0.4 |
| Olive oil | 0.1 | 0.1 | 0.1 | 0.1 | 0.1 | 0.1 | 0.1 |
| Polyoxyethylene(2) cetyl ether | 4 | 4 | 4 | 4 | 4 | 4 | 4 |
| Polyoxyethylene(5,5) cetyl ether | 2 | 2 | 2 | 2 | 2 | 2 | 2 |
| Polyoxyethylene(30) cetyl ether | 5 | 5 | 5 | 5 | 5 | 5 | 5 |
| Oleic acid | 1 | 2 | 0 | 0.3 | 1 | 1 | 1 |
| Oleyl alcohol | 1 | 0 | 2 | 0.3 | 1 | 1 | 1 |
| Stearic acid | 0 | 0 | 0 | 0 | 0 | 0 | 0 |
| Hexyldecanol | 2 | 2 | 2 | 2 | 2 | 2 | 2 |
| Cetostearyl alcohol | 7 | 7 | 7 | 7 | 7 | 7 | 7 |
| N-methacryloxyethyl N,N-dimethylammonium-o-N-methylcarboxy betaine/alkyl methyacrylate copolymer | 0.1 | 0.1 | 0.1 | 0.1 | 0.1 | 0.1 | 0.1 |
| Aminoethylaminoproply-methylsiloxane/dimethylsiloxane copolymer | 0.1 | 0.1 | 0.1 | 0.1 | 0.1 | 0.1 | 0.1 |
| 1,3-Butylene glycol | 3 | 3 | 3 | 3 | 3 | 3 | 3 |
| Trisodium ethylene-diamine hydroxyethyl triacetate dihydrate | 0.2 | 0.2 | 0.2 | 0.2 | 0.2 | 0.2 | 0.2 |
| Anhydrous sodium sulfite | 0.1 | 0.1 | 0.1 | 0.1 | 0.1 | 0.1 | 0.1 |
| Ammonium chloride | 1.5 | 1.5 | 1.5 | 1.5 | 1.5 | 1.5 | 1.5 |
| Strong ammonia water (20%) | 6 | 6 | 6 | 6 | 6 | 6 | 6 |
| Fragrance | proper amount | proper amount | proper amount | proper amount | proper amount | proper amount | proper amount |
| Purified water | balance | balance | balance | balance | balance | balance | balance |
| | 100 | 100 | 100 | 100 | 100 | 100 | 100 |
| Component (B) When Mixed | 0.2 | 0.2 | 0.2 | 0.2 | 0.2 | 0.2 | 0.2 |
| Component (D) When Mixed | 5.5 | 5.5 | 5.5 | 5.5 | 5.5 | 5.5 | 5.5 |
| (D)/(B) When Mixed | 27.5 | 27.5 | 27.5 | 27.5 | 27.5 | 27.5 | 27.5 |
| Component (C) When Mixed | 2.95 | 2.95 | 2.95 | 2.95 | 2.95 | 2.95 | 2.95 |
| Evaluation (Texture During Washing Off) | A | A | A | A | A | B | A |
| Evaluation (Texture After Drying) | A | B | B | B | A | A | A |

| Component | Example 8 | Example 9 | Example 10 | Example 11 | Example 12 | Example 13 |
|---|---|---|---|---|---|---|
| Hydroxyethyl cellulose dimethyl diallyl ammonium chloride | 0.1 | 0.1 | 0.1 | 0.1 | 0.1 | 0.1 |
| Dimethyl diallyl ammonium chloride polymer | 0 | 0 | 0 | 0 | 0 | 0 |
| Xanthan gum | 0 | 0 | 0 | 0 | 0 | 0 |
| Cetyltrimethylammonium chloride | 0.2 | 0.15 | 0.8 | 0.1 | 0.4 | 0.4 |
| Behenyltrimethylammonium chloride | 0 | 0 | 0 | 0 | 0 | 0 |
| Cetrimonium methosulfate | 0 | 0 | 0 | 0 | 0 | 0 |
| Sodium polyoxyethylene lauryl ether sulfate | 0 | 0 | 0 | 0 | 0 | 0 |
| Liquid isoparaffin | 4 | 4 | 4 | 4 | 1 | 5.0 |
| Paraffin | 0 | 0 | 0 | 0 | 0 | 0 |
| Cetyl 2-ethylhexanoate | 1 | 1 | 1 | 1 | 0.5 | 0 |
| Myristyl myrisate | 0 | 0 | 0 | 0 | 0 | 0 |
| Beeswax | 0.4 | 0.4 | 0.4 | 0.4 | 0.1 | 0 |
| Lanolin | 0.4 | 0.4 | 0.4 | 0.4 | 0.1 | 0 |
| Olive oil | 0.1 | 0.1 | 0.1 | 0.1 | 0.1 | 0 |
| Polyoxyethylene(2) cetyl ether | 2 | 4 | 2 | 4 | 4 | 4 |
| Polyoxyethylene(5,5) cetyl ether | 1 | 2 | 1 | 2 | 2 | 2 |
| Polyoxyethylene(30) cetyl ether | 2.5 | 5 | 2.5 | 5 | 5 | 5 |
| Oleic acid | 1 | 1 | 1 | 1 | 1 | 1 |
| Oleyl alcohol | 1 | 1 | 1 | 1 | 1 | 1 |
| Stearic acid | 0 | 0 | 0 | 0 | 0 | 0 |
| Hexyldecanol | 2 | 2 | 2 | 2 | 2 | 2 |

TABLE 1-continued

| | | | | | | |
|---|---|---|---|---|---|---|
| Cetostearyl alcohol | 7 | 7 | 7 | 7 | 7 | 7 |
| N-methacryloxyethyl N,N-dimethylammonium-o-N-methylcarboxy betaine/alkyl methyacrylate copolymer | 0.1 | 0.1 | 0.1 | 0.1 | 0.1 | 0.1 |
| Aminoethylaminopropyl-methylsiloxane/dimethylsiloxane copolymer | 0.1 | 0.1 | 0.1 | 0.1 | 0.1 | 0.1 |
| 1,3-Butylene glycol | 3 | 3 | 3 | 3 | 3 | 3 |
| Trisodium ethylene-diamine hydroxyethyl triacetate dihydrate | 0.2 | 0.2 | 0.2 | 0.2 | 0.2 | 0.2 |
| Anhydrous sodium sulfite | 0.1 | 0.1 | 0.1 | 0.1 | 0.1 | 0.1 |
| Ammonium chloride | 1.5 | 1.5 | 1.5 | 1.5 | 1.5 | 1.5 |
| Strong ammonia water (20%) | 6 | 6 | 6 | 6 | 6 | 6 |
| Fragrance | proper amount | proper amount | proper amount | proper amount | proper amount | proper amount |
| Purified water | balance | balance | balance | balance | balance | balance |
| | 100 | 100 | 100 | 100 | 100 | 100 |
| Component (B) When mixed | 0.1 | 0.075 | 0.4 | 0.05 | 0.2 | 0.2 |
| Component (D) When mixed | 2.75 | 5.5 | 2.75 | 5.5 | 5.5 | 5.5 |
| (D)/(B) When Mixed | 2.75 | 73.3 | 6.875 | 110 | 27.5 | 27.5 |
| Component (C) When Mixed | 2.95 | 2.95 | 2.95 | 2.95 | 0.9 | 2.95 |
| Evaluation (Texture During Washing Off) | A | A | B | A | B | B |
| Evaluation (Texture After Drying) | A | A | B | B | B | B |

TABLE 2

| | Component | Comparative Example 1 | Comparative Example 2 | Comparative Example 3 | Comparative Example 4 | Comparative Example 5 |
|---|---|---|---|---|---|---|
| (A) | Hydroxyethyl cellulose dimethyl diallyl ammonium chloride | 0.1 | 0 | 0.4 | 0.1 | 0.4 |
| (A) | Acrylamide/acrylic acid/dimethyl diallyl ammonium chloride copolymer solution | 0 | 0 | 0 | 0 | 0 |
| (a) | Xanthan gum | 0 | 0.1 | 0 | 0 | 0 |
| (B) | Cetyltrimethylammonium chloride | 0.4 | 0.4 | 0 | 12.4 | 0.4 |
| (B) | Behenyltrimethylammonium chloride | 0 | 0 | 0 | 0 | 0 |
| (b) | Sodium polyoxyethylene lauryl ether sulfate | 0 | 0 | 0.4 | 0 | 0 |
| (C) | Liquid isoparaffin | 4 | 4 | 0 | 4 | 0 |
| (C) | Paraffin | 0 | 0 | 5 | 0 | 0 |
| (C) | Cetyl 2-ethylhexanoate | 1 | 1 | 0 | 1 | 0 |
| (C) | Myristyl myristate | 0 | 0 | 0.4 | 0 | 0 |
| (C) | Beeswax | 0.4 | 0.4 | 0.1 | 0.4 | 0 |
| (C) | Lanolin | 0.4 | 0.4 | 0.2 | 0.4 | 0 |
| (C) | Olive oil | 0.1 | 0.1 | 0 | 0.1 | 0 |
| (D) | Polyoxyethylene(2) cetyl ether | 4 | 4 | 4 | 0 | 4 |
| (D) | Polyoxyethylene(5,5) cetyl ether | 2 | 2 | 2 | 0 | 2 |
| (D) | Polyoxyethylene(30) cetyl ether | 5 | 5 | 5 | 0 | 5 |
| (E) | Oleic acid | 0 | 1 | 1 | 1 | 1 |
| (E) | Oleyl alcohol | 0 | 1 | 1 | 1 | 1 |
| (e) | Stearic acid | 2 | 0 | 0 | 0 | 0 |
| | Hexyldecanol | 2 | 2 | 2 | 2 | 2 |
| | Cetostearyl alcohol | 7 | 7 | 7 | 7 | 7 |
| | N-methacryloxyethyl N,N-dimethylammonium-o-N-methylcarboxy betaine/alkyl methyacrylate copolymer | 0.1 | 0.1 | 0.1 | 0.1 | 0.1 |
| | Aminoethylaminopropyl-methylsiloxane/dimethylsiloxane copolymer | 0.1 | 0.1 | 0.1 | 0.1 | 0.1 |
| | 1,3-Butylene glycol | 3 | 3 | 3 | 3 | 3 |
| | Trisodium ethylene-diamine hydroxyethyl triacetate dihydrate | 0.2 | 0.2 | 0.2 | 0.2 | 0.2 |
| | Anhydrous sodium sulfite | 0.1 | 0.1 | 0.1 | 0.1 | 0.1 |
| | Ammonium chloride | 1.5 | 1.5 | 1.5 | 1.5 | 1.5 |
| | Strong ammonia water | 6 | 6 | 6 | 6 | 6 |

TABLE 2-continued

| Component | Comparative Example 1 | Comparative Example 2 | Comparative Example 3 | Comparative Example 4 | Comparative Example 5 |
|---|---|---|---|---|---|
| Fragrance | proper amount | proper amount | proper amount | proper amount | proper amount |
| Purified water | balance | balance | balance | balance | balance |
|  | 100 | 100 | 100 | 100 | 100 |
| Component (B) When Mixed | 0.2 | 0.2 | 0 | 0.2 | 0.2 |
| Component (D) When Mixed | 5.5 | 5.5 | 5.5 | 0 | 5.5 |
| (D)/(B) When Mixed | 27.5 | 27.5 | 0 | 0 | 27.5 |
| Component (C) When Mixed | 2.95 | 2.95 | 0.15 | 2.95 | 0 |
| Evaluation (Texture During Washing Off) | C | D | C | C | C |
| Evaluation (Texture After Drying) | C | D | C | C | C |

Examples 15 to 28 and Comparative Examples 6 to 10 were prepared by adding an oxidation dye (0.1 mass % p-phenylenediamine, 0.3 mass % resorcinol, 0.05 mass % p-aminophenol, 0.05 mass % 5-amino-o-cresol and 0.03 mass % 2,4-diaminophenoxy ethanol hydrochloride) to the respective Examples and Comparative Examples and evaluated. As a result, the effects of the invention were independent of the presence or absence of the oxidation dye, and results equivalent to those of Examples 1 to 14 and Comparative Examples 1 to 5 were obtained.

According to the invention, a hair color which achieves excellent texture consistently from during plain rinsing in the treatment with the hair color to the dry state after the treatment is provided.

The invention claimed is:

1. A hair cosmetic composition, comprising the following components (A) to (E), and containing no silicones:

(A) one or more cationic polymers having diallyl quaternary ammonium salt unit;

(B) one or more cationic surfactants selected from cetyltrimethyl ammonium chloride and behenyltrimethyl ammonium chloride;

(C) one or more selected from hydrocarbon oils, ester oils, waxes and vegetable oils;

(D) one or more nonionic surfactants selected from polyoxyethylene (2-30) alkyl ethers; and (E) one or more selected from oleyl alcohol and oleic acid.

2. A method of treating hair, comprising applying thereto the composition of claim 1.

* * * * *